US010393000B2

(12) United States Patent
Imaoka et al.

(10) Patent No.: US 10,393,000 B2
(45) Date of Patent: Aug. 27, 2019

(54) FAILURE DETERMINATION APPARATUS FOR OXYGEN CONCENTRATION SENSOR

(71) Applicant: MITSUBISHI JIDOSHA KOGYO KABUSHIKI KAISHA, Tokyo (JP)

(72) Inventors: Kenta Imaoka, Anjo (JP); Junya Kitada, Okazaki (JP); Hideo Matsunaga, Okazaki (JP)

(73) Assignee: MITSUBISHI JIDOSHA KOGYO KABUSHIKI KAISHA, Tokyo (JP)

( * ) Notice: Subject to any disclaimer, the term of this patent is extended or adjusted under 35 U.S.C. 154(b) by 296 days.

(21) Appl. No.: 14/935,624

(22) Filed: Nov. 9, 2015

(65) Prior Publication Data

US 2016/0186637 A1 Jun. 30, 2016

(30) Foreign Application Priority Data

Dec. 24, 2014 (JP) .................................. 2014-261131

(51) Int. Cl.
*F01N 11/00* (2006.01)
*F01N 3/20* (2006.01)
(Continued)

(52) U.S. Cl.
CPC .............. *F01N 11/007* (2013.01); *F01N 3/20* (2013.01); *F02D 41/126* (2013.01);
(Continued)

(58) Field of Classification Search
CPC ...... F01N 11/007; F01N 3/20; F01N 2550/00; F01N 2560/025; F01N 2900/1402;
(Continued)

(56) References Cited

U.S. PATENT DOCUMENTS 5,154,055 A * 10/1992 Nakane ................. F01N 11/007
60/276
5,743,082 A * 4/1998 Matsumoto ........ B01D 53/8696
60/274

(Continued)

FOREIGN PATENT DOCUMENTS

JP 3676641 B2 7/2005
JP 4548443 B2 9/2010

*Primary Examiner* — Laert Dounis
*Assistant Examiner* — Matthew T Largi
(74) *Attorney, Agent, or Firm* — Birch, Stewart, Kolasch & Birch, LLP (57) ABSTRACT

A failure determination apparatus for an oxygen concentration sensor disposed downstream of a catalyst provided in an exhaust system is provided for detecting a failure in the oxygen concentration sensor. The failure determination apparatus comprises: a failure determination device for determining a failure in the oxygen concentration sensor based on the length of a period when the output of the oxygen concentration sensor passes through a predetermined output section during enrichment control after a fuel cut mode of the internal combustion engine is released; a rich fuel supply amount calculation device for calculating the time average of an enriching fuel supply amount, relative to a fuel supply amount necessary for stoichiometric combustion, based on an actual fuel supply amount during the enrichment control; and a failure determination restriction device for restricting failure determination of the failure determination device based on the time average of the enriching fuel supply amount.

7 Claims, 5 Drawing Sheets

(51) Int. Cl.
  *F02D 41/12* (2006.01)
  *F02D 41/14* (2006.01)
  *G01N 27/417* (2006.01)

(52) U.S. Cl.
  CPC ..... *F02D 41/1495* (2013.01); *G01N 27/4175* (2013.01); *F01N 2550/00* (2013.01); *F01N 2560/025* (2013.01); *F01N 2900/1402* (2013.01); *F02D 41/1454* (2013.01); *Y02T 10/47* (2013.01)

(58) Field of Classification Search
  CPC ............... F02D 41/126; F02D 41/1495; F02D 41/1454; G01N 27/4175
  See application file for complete search history.

(56) References Cited

U.S. PATENT DOCUMENTS

| | | | | |
|---|---|---|---|---|
| 6,338,243 | B1* | 1/2002 | Takaoka | F01N 3/0814 60/276 |
| 6,698,187 | B2* | 3/2004 | Nishioka | F01N 3/0842 60/277 |
| 6,804,951 | B2* | 10/2004 | Nader | F01N 11/007 60/274 |
| 6,874,313 | B2* | 4/2005 | Yurgil | F01N 11/007 123/198 F |
| 2007/0214775 | A1* | 9/2007 | I | F01N 3/101 60/288 |
| 2008/0110447 | A1* | 5/2008 | Wakahara | F02D 41/1438 123/672 |

\* cited by examiner

FAILURE DETERMINATION APPARATUS FOR OXYGEN CONCENTRATION SENSOR

The entire disclosure of Japanese Patent Application No. 2014-261131 filed on Dec. 24, 2014 is expressly incorporated by reference herein.

TECHNICAL FIELD

This invention relates to a failure determination apparatus for an oxygen concentration sensor, the apparatus determining whether or not there is a failure in an oxygen concentration sensor disposed downstream of a catalyst provided in an exhaust system of an internal combustion engine.

BACKGROUND ART

The exhaust system of an engine (internal combustion engine) is usually equipped with a catalyst, such as a three-way catalyst or a NOx storage catalyst, for purification of exhaust. Downstream of the catalyst, an oxygen concentration sensor may be provided for exercising air-fuel ratio control.

A technology for switching the fuel injection mode of the internal combustion engine according to load or the like is also known. The fuel injection mode includes a normal operation mode in which an operation is performed in a stoichiometric or lean state, for example, with the air-fuel ratio of the exhaust being provided as a feedback; an enriched operation mode in which the air-fuel ratio is subjected to open loop control for enrichment in the case of a high load or the like; and a fuel cut mode in which fuel injection is stopped under no-load conditions such as during deceleration.

A proposal has been made for a method which, in failure determination for detecting the deterioration of an oxygen concentration sensor with the use of enrichment after release of the fuel cut mode, prohibits monitoring if an exhaust gas flow rate integrated value is less than a predetermined amount (see Japanese Patent No. 3676641).

A proposal has also been made for a method which comprises detecting a failure from an output of an oxygen sensor when controlling a target air-fuel ratio during travel from a lean value to a rich value (see Japanese Patent No. 4548443).

SUMMARY OF THE INVENTION

Problems to Be Solved By the Invention

With the above-described technologies, however, the actual air-fuel ratio may fail to be rich, against expectations, owing to learning of a fuel correction amount or transient changes in an intake air amount. In this case, even if the flow rate is great, the oxygen concentration sensor delays in responding, arousing a possibility for determining erroneously that a failure has occurred.

The present invention has been accomplished in the light of the above circumstances. It is an object of the invention to provide a failure determination apparatus for an oxygen concentration sensor which detects a failure in the oxygen concentration sensor with high accuracy while preventing an erroneous determination of the failure.

Means for Solving the Problems

A first aspect of the present invention, for attaining the above object, is a failure determination apparatus for an oxygen concentration sensor disposed downstream of a catalyst provided in an exhaust system of an internal combustion engine, comprising: a failure determination device for determining a failure in the oxygen concentration sensor based on a length of a period when an output of the oxygen concentration sensor passes through a predetermined output section during enrichment control of an exhaust air-fuel ratio which is performed after a fuel cut mode of the internal combustion engine is released, or based on a length of a period until the output of the oxygen concentration sensor during the enrichment control after release of the fuel cut mode reaches a predetermined output; a rich fuel supply amount calculation device for calculating a time average of an enriching fuel supply amount, which is necessary for enrichment of the exhaust air-fuel ratio, relative to a fuel supply amount necessary for stoichiometric combustion of the internal combustion engine, based on an actual fuel supply amount during the enrichment control; and a failure determination restriction device for restricting failure determination of the failure determination device based on the time average of the enriching fuel supply amount.

According to such an aspect, the failure determination of the failure determination device is restricted based on the time average of the enriching fuel supply amount relative to the fuel supply amount necessary for stoichiometric combustion, the time average being calculated from the actual fuel supply amount during the enrichment control. By so doing, erroneous determination of the failure in the oxygen concentration sensor can be prevented.

A second aspect of the present invention is the failure determination apparatus for an oxygen concentration sensor according to the first aspect, wherein the failure determination restriction device restricts the failure determination of the failure determination device if the time average of the enriching fuel supply amount is equal to or less than a predetermined value.

According to such an aspect, erroneous determination of a failure in the oxygen concentration sensor is prevented by restricting the failure determination of the failure determination device if the time average of the enriching fuel supply amount is equal to or less than a predetermined value.

A third aspect of the present invention is the failure determination apparatus for an oxygen concentration sensor according to the first or second aspect, wherein the failure determination device determines the failure if the length of the period when the output of the oxygen concentration sensor during the enrichment control passes through the predetermined output section is greater than a predetermined failure determination value.

According to such an aspect, a failure determination is made if the length of the period when the output of the oxygen concentration sensor during the enrichment control passes through the predetermined output section is greater than a predetermined failure determination value. Thus, the failure can be determined with high accuracy.

A fourth aspect of the present invention is the failure determination apparatus for an oxygen concentration sensor according to the third aspect, wherein the failure determination restriction device sets the failure determination value of the failure determination device to be high if the time average of the enriching fuel supply amount is equal to or less than a predetermined value.

According to such an aspect, the failure determination of the failure determination device is restricted by setting the failure determination value of the failure determination device to be high if the time average of the enriching fuel supply amount is equal to or less than the predetermined value. By so doing, the erroneous determination of the failure in the oxygen concentration sensor is prevented.

Effects of the Invention

According to the present invention described above, erroneous determination of a failure in the oxygen concentration sensor can be prevented by restricting the failure determination of the failure determination device based on the time average of the enriching fuel supply amount relative to the fuel supply amount necessary for stoichiometric combustion, which is calculated from the actual fuel supply amount during the enrichment control.

BRIEF DESCRIPTION OF THE DRAWINGS

FIG. 1 is a schematic configuration diagram of an intake/exhaust system of an engine which a failure determination apparatus according to the present invention is applied to.

MODE FOR CARRYING OUT THE INVENTION

The present invention will now be described in detail based on its embodiments.

Embodiment 1

Figure 1:
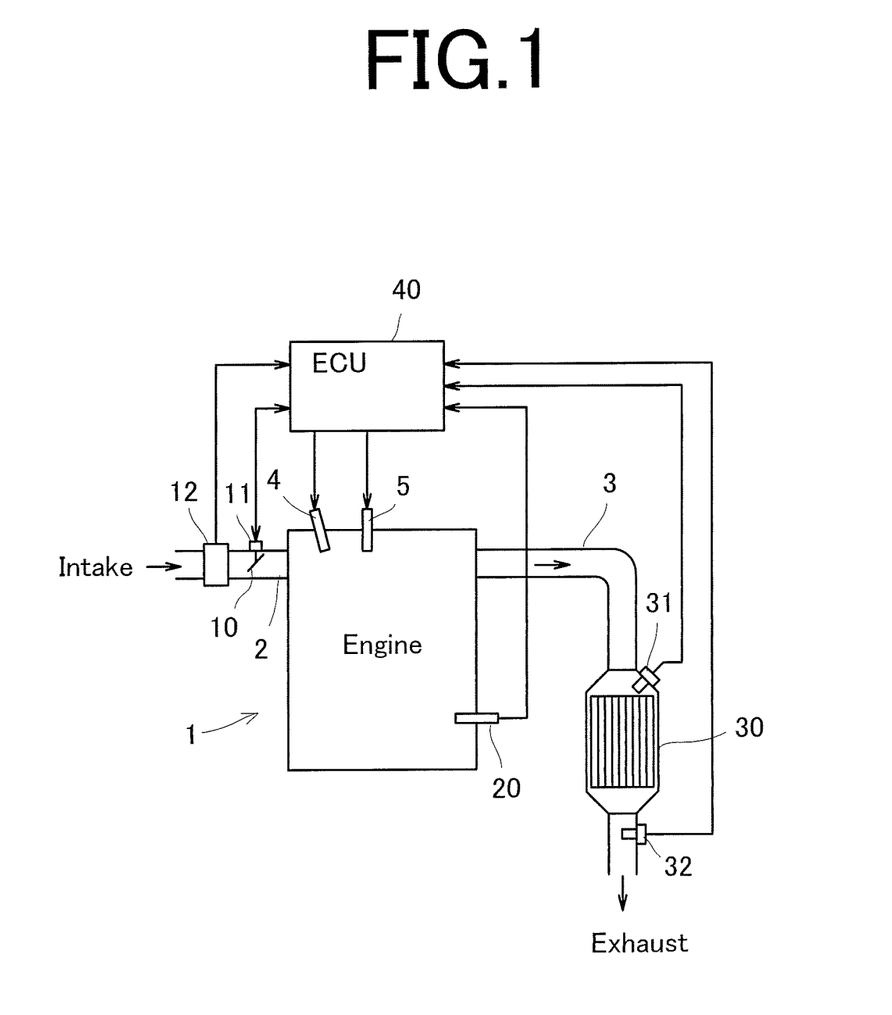

FIG. 1 shows a schematic configuration diagram of an intake/exhaust system of an engine 1 (internal combustion engine) to which a failure determination apparatus according to the present invention is applied.

The engine 1 is a gasoline engine of a cylinder fuel injection type for directly injecting fuel, for example, from an injection value into a cylinder.

As shown in FIG. 1, an electronic controlled throttle valve 10 for adjusting the flow rate of intake air is provided in an intake passage 2 of the engine 1. The throttle valve 10 is equipped with a throttle position sensor 11 for detecting the opening degree of the throttle valve 10.

An air flow sensor 12 for detecting the intake flow rate is provided in a part of the intake passage 2 upstream of the throttle valve 10.

Moreover, the engine 1 is provided with a crank angle sensor 20 for detecting a crank angle, and other sensors (not shown) for detecting the operating status of the engine 1, such as a cam angle sensor and a water temperature sensor.

An exhaust purification catalyst 30 such as a three-way catalyst is interposed in an exhaust passage 3 of the engine 1.

An upstream side oxygen concentration sensor 31 for detecting the oxygen concentration of exhaust flowing into the exhaust purification catalyst 30 is provided on the upstream side of the exhaust purification catalyst 30. A downstream side oxygen concentration sensor (air-fuel ratio detection device) 32 for detecting the oxygen concentration of the exhaust after passing through the exhaust purification catalyst 30 is provided on the downstream side of the exhaust purification catalyst 30.

An ECU 40 is a control device for exercising the integrated control, including operation control, of the engine 1, and comprises input/output devices, storage devices (ROM, RAM, non-volatile RAM, etc.), a central processing unit, and so on.

The input side of the ECU 40 receives the input of detected information from the above-mentioned throttle position sensor 11, air flow sensor 12, crank angle sensor 20, upstream side oxygen concentration sensor 31, and downstream side oxygen concentration sensor 32, and other sensors (not shown) for detecting the operating state of the engine 1 and the vehicle, such as the water temperature sensor, an accelerator position sensor for detecting the opening of an accelerator, and a vehicle speed sensor.

To the output side of the ECU 40, various output devices are connected, such as the throttle valve 10, a fuel injection valve 4, and an ignition plug 5. The ECU 40 computes a target throttle opening, a target fuel injection amount, a target fuel injecting timing, a target ignition timing, etc. based on detected information from the various sensors, and outputs these data to the various output devices, thereby controlling the throttle valve 10, fuel injection valve 4, etc.

The ECU 40, in particular, switches the fuel injection mode of the engine 1 according to load or the like. The fuel injection mode includes a normal operation mode (second operation mode) in which an operation is performed, with the air-fuel ratio of the exhaust being provided as a feedback, so that a stoichiometric state or a lean state, for example, is attained; an enriched operation mode (first operation mode) in which the air-fuel ratio is open loop-controlled so as to be enriched in the case of a high load or the like; and a fuel cut mode (third operation mode) in which fuel injection is stopped under no-load conditions such as during deceleration. In the normal operation mode, a feedback operation is performed based on the outputs of the upstream side oxygen concentration sensor 31 and the downstream side oxygen concentration sensor 32. In the enriched operation mode and the fuel cut mode, an open loop operation is performed.

The ECU 40 also has the function of determining a failure in the downstream side oxygen concentration sensor 32.

Determination of a failure in the downstream side oxygen concentration sensor 32 is performed as follows: When the operation mode is shifted to the fuel cut mode during the operation of the engine, fuel injection is stopped (fuel is cut). At this time, there is a change in the air-fuel ratio of the exhaust detected by the downstream side oxygen concentration sensor 32. Based on this change, whether or not the downstream side oxygen concentration sensor 32 has failed is determined (failure determination device).

Concretely, the failure determination device finds a period when the output of the downstream side oxygen concentration sensor 32 during enrichment control after release of the fuel cut mode of the engine 1 passes through a predetermined output section, for example, a period from 0.3V to 0.5V, and if the period is greater than a predetermined value, determines that a failure has occurred in the downstream side oxygen concentration sensor 32.

Determination of failure is not limited to the above manner, but may be made based on a period until the output of the downstream side oxygen concentration sensor 32 during enrichment control after release of the fuel cut mode of the engine 1 reaches a predetermined output. For example, if the length of the period when the output reaches 0.3V or 0.5V after release of the fuel cut mode is greater than a predetermined value, a failure may be determined. Alternatively, it is determined whether the output of the downstream side oxygen concentration sensor 32 at the time of passage of a predetermined period, for example, a predetermined number of ignitions of the order of 150 ignitions after release, has reached a predetermined value. If the output does not reach the predetermined value, a failure may be determined.

Figure 2:
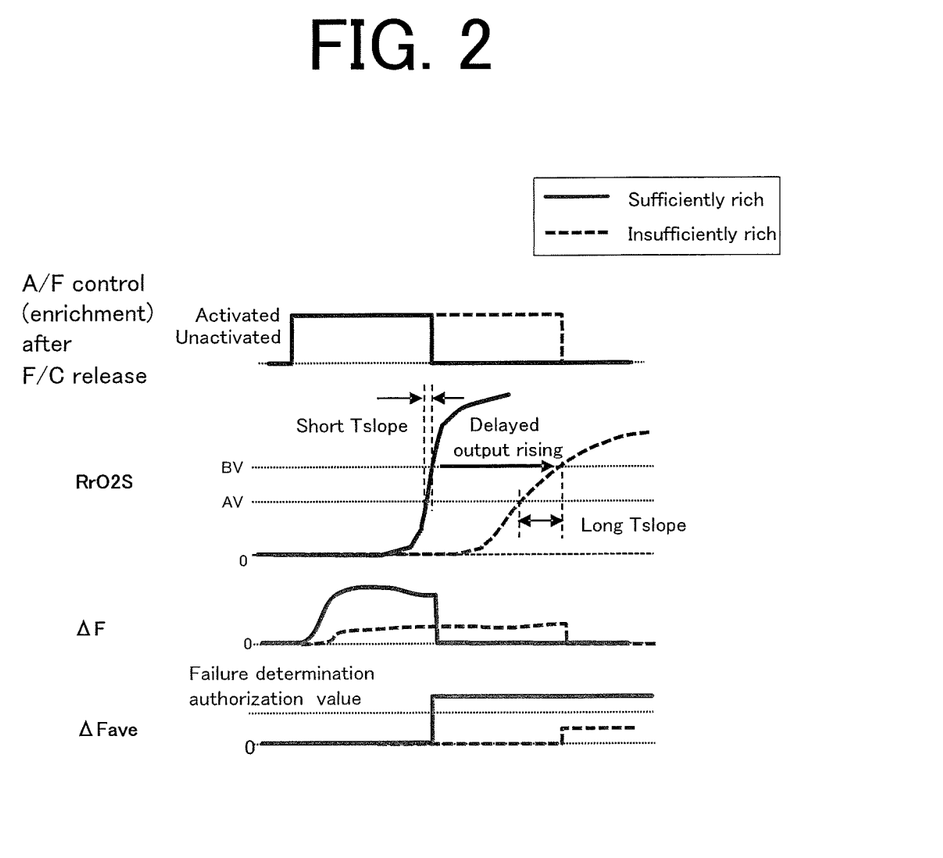
FIG. 2 is a time chart showing Embodiment 1.

FIG. 2 is a time chart showing an example of changes in the output value V of the downstream side oxygen concentration sensor 32 in the enrichment control mode after release of the fuel cut mode, changes in a fuel supply amount added by enrichment (called an enriching fuel supply amount), $\Delta F$, relative to the fuel supply amount necessary for stoichiometric combustion, and changes in the time average $\Delta Fave$ of $\Delta F$. In the drawing, solid lines represent cases where enrichment has been performed normally, and dashed or broken lines represent cases where the parameters do not become rich, unlike target values, owing to the learning of a fuel correction amount or transient changes in the air intake amount.

When fuel is cut (F/C) from an air-fuel ratio feedback operation in the normal operation mode, the output value V of the downstream side oxygen concentration sensor 32 begins to lower with a time lag after start of the fuel cut, and the output comes to 0V. As indicated by a solid line in FIG. 2, however, when the fuel cut mode is released to enter the enrichment control mode (A/F control (enrichment)), the output value V rises with a time lag to complete the enrichment control. At this time, a required time Tslope for the output value of the downstream side oxygen concentration sensor 32 to achieve the corresponding rise, concretely, to change by a predetermined range A-B (e.g., change from 0.3V to 0.5V), takes a nearly constant value. Moreover, a period from the release of the fuel cut mode until the output value V of the downstream side oxygen concentration sensor 32 rises to a predetermined value, for example, to 0.3V or 0.5V, namely, a required time, also takes a nearly constant value.

The failure determination device of the ECU 40 measures this required time Tslope. If the measured value is equal to or lower than a preset threshold value, the failure determination device determines that the downstream side oxygen concentration sensor 32 is normal. If the above value exceeds the threshold value, the failure determination device determines that the downstream side oxygen concentration sensor 32 is suffering from a failure. In place of the required time Tslope, it is permissible, for example, to measure a required time until the rise to 0.3V or 0.5V. If the measured required time is equal to or lower than a preset threshold value, it may be determined that the downstream side oxygen concentration sensor 32 is normal. If the measured required time exceeds the threshold value, it may be determined that the downstream side oxygen concentration sensor 32 is failed. Moreover, if, after release of the fuel cut mode, the value rises to, say, 0.5V during a preset required time, it may be determined that the downstream side oxygen concentration sensor 32 is normal. If the value does not rise to 0.5V during the preset required time, on the other hand, it may be determined that the downstream side oxygen concentration sensor 32 is normal, or if the value exceeds the threshold value, it may be determined that the downstream side oxygen concentration sensor 32 is failed.

In the present embodiment, moreover, there is provided the function of restricting the determination of a failure in the downstream side oxygen concentration sensor 32 if enrichment is insufficient in the enrichment control mode after release of the fuel cut mode.

As indicted by the broken lines in FIG. 2, if enrichment is insufficient despite execution of enrichment control after release of the fuel cut mode, the rising of the output value of the downstream side oxygen concentration sensor 32 is delayed, and the degree of the rise is low. Concretely, the required time Tslope for the output value V of the downstream side oxygen concentration sensor 32 to change by the predetermined range A-B (for example, from 0.3V to 0.5V) lengthens. Furthermore, the required time until the output value V of the downstream side oxygen concentration sensor 32 rises to a predetermined value, e.g., 0.3V or 0.5V, after release of the fuel cut mode also extends. Hence, there is a possibility for erroneous determination that the downstream side oxygen concentration sensor 32 has a failure.

Thus, the ECU 40 calculates the time average of a rich fuel supply amount ($\Delta Fave$), which is the time average of the enriching fuel supply amount relative to the fuel supply amount necessary for stoichiometric combustion, from the actual fuel supply amount during the enrichment control after the fuel cut mode release (rich fuel supply amount calculation device). If the time average of the rich fuel supply amount is smaller than a preset threshold value, determination of a failure in the downstream side oxygen concentration sensor 32 is prohibited (failure determination prohibition device). The actual fuel supply amount is obtained by computing a fuel injection amount per unit time from the driving time of the fuel injector and the engine speed. A surplus fuel amount per unit time relative to stoichiometric combustion, namely, the rich fuel supply amount $\Delta F$, is calculated from the computed fuel injection amount and the air-fuel ratio A/F.

Such a rich fuel supply amount $\Delta F$ becomes large during enrichment control and, upon completion of the enrichment control, drops to zero, while the time average $\Delta Fave$ takes a constant value when the enrichment is finished, as indicated by the solid lines in FIG. 2.

As indicated by the broken lines in FIG. 2, on the other hand, if enrichment is insufficient, the rich fuel supply amount $\Delta F$ is smaller than when the enrichment is sufficient, and the time average $\Delta Fave$ is also smaller. These phenomena are ascribed to the learning of the fuel correction amount and transient changes in the intake air amount. Accordingly, if the time average of the rich fuel supply amount, $\Delta Fave$, is smaller than a failure determination authorization set value which is a threshold value set to be lower than the value of $\Delta Fave$ when enrichment is normal, failure determination is prohibited (failure determination prohibition device). If enrichment is sufficient, $\Delta Fave$ is greater than the failure determination authorization set value, and failure determination is authorized.

Figure 3:
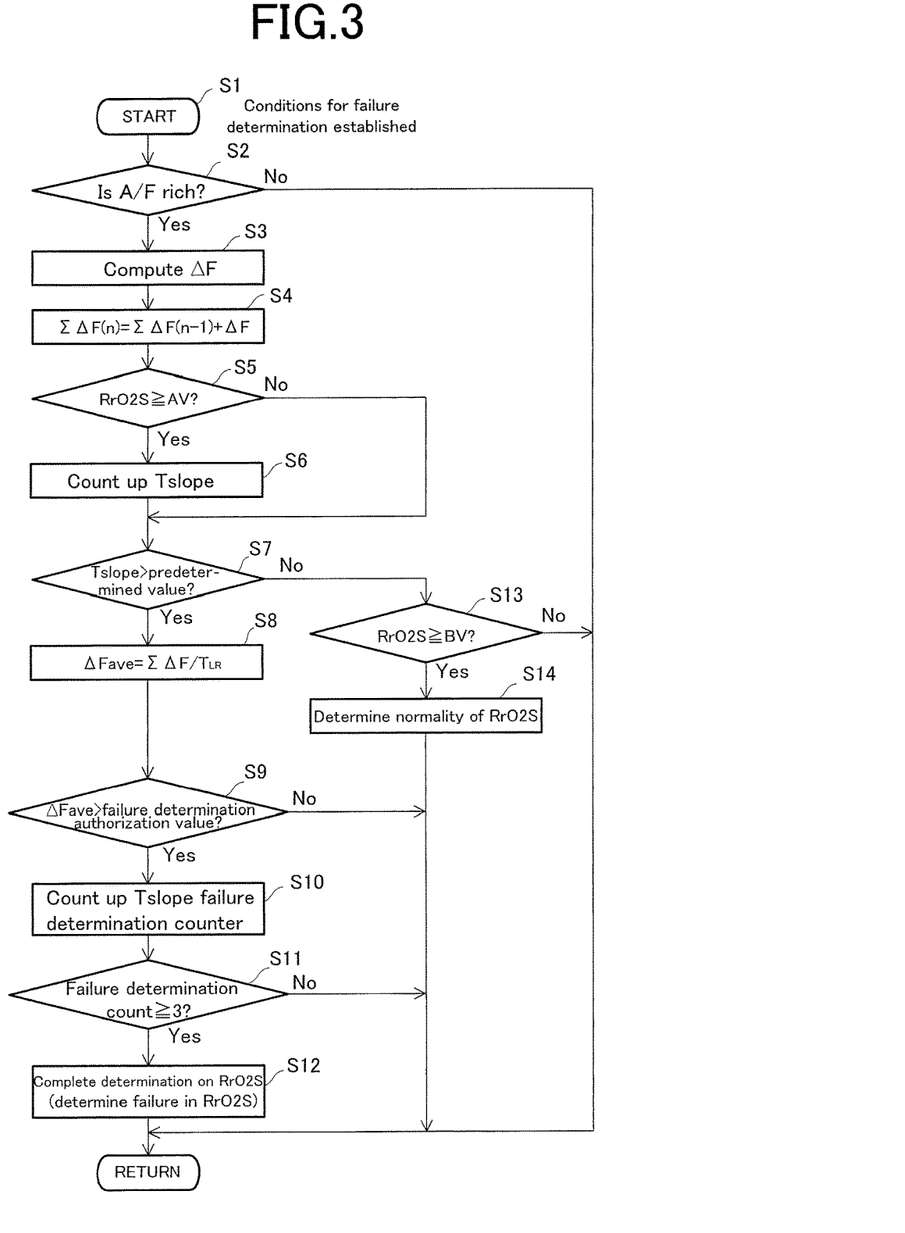
FIG. 3 is a flow chart of Embodiment 1.

The flow of failure determination according to the present embodiment will be described by reference to FIG. 3. As shown in FIG. 3, when conditions for failure determination are established in Step S1, it is determined in Step S2 whether the air-fuel ratio A/F is rich. If A/F is rich (Step S2: Yes), $\Delta F$ is computed in Step S3. As stated earlier, $\Delta F$ is obtained by computing the fuel injection amount per unit time from the driving time of the fuel injector and the engine speed, and finding a surplus fuel amount per unit time relative to stoichiometric combustion from the computed fuel injection amount and the air-fuel ratio A/F. If A/F is not rich (Step S2: No), the program is terminated automatically.

Then, in Step S4, $\Sigma\Delta F(n)$ is obtained. $\Sigma\Delta F(n)$ is the integrated value of $\Delta F$, and $\Sigma\Delta F(n)=\Sigma\Delta F(n-1)+\Delta F$. Then, in Step S5, it is determined whether the output of the downstream side oxygen concentration sensor 32, RrO2S, is equal to or more than a predetermined value AV, e.g., 0.3V. If RrO2S is equal to or more than the predetermined value AV (Step S5: Yes), Tslope is counted up in Step S6, and it is determined in Step S7 whether Tslope is greater than a predetermined value. If, in Step S5, the output RrO2S of the downstream side oxygen concentration sensor 32 is less than the predetermined value AV (Step S5: No), the program proceeds to Step S7 to determine whether Tslope is greater than the predetermined value.

If Tslope is greater than the predetermined value (Step S7: Yes), the time average ΔFave of ΔF is computed in Step S8. If a required time from the start of computation of ΔF until Tslope exceeds 0.5 sec is designated as TLR, ΔFave=ΣΔF(n)/TLR.

If, in Step S9, ΔFave is larger than the failure determination authorization value (Step S9: Yes), a Tslope failure determination counter is counted up in Step S10. In Step S11, it is determined whether the failure determination count is equal to or more than 3. If the failure determination count is equal to or more than 3 (Step S11: Yes), it is determined in Step S12 that the downstream side oxygen concentration sensor 32 is failed. At this stage, the program terminates. If the failure determination count is smaller than 3 (Step S11: No), the program automatically ends, without determining that the downstream side oxygen concentration sensor 32 is failed.

If Tslope is equal to or less than the predetermined value (Step S7: No), it is determined in Step S13 whether the output RrO2S of the downstream side oxygen concentration sensor 32 is equal to or more than a predetermined value BV, e.g., 0.5V. If RrO2S is equal to or more than the predetermined value BV (Step S13: Yes), it is determined in Step S14 that the downstream side oxygen concentration sensor 32 is normal. At this stage, the program terminates. If RrO2S is less than the predetermined value BV (Step S13: No), the program ends automatically.

If, in Step S9, ΔFave is equal to or smaller than the failure determination authorization value (Step S9: No), failure determination is prohibited to bring the program to an end.

According to the flow described above, even when Tslope is larger than the predetermined value, failure determination is not authorized, unless ΔFave is more than the failure determination authorization value. If ΔFave is equal to or smaller than the failure determination authorization value, a determination of a failure is prohibited.

As described above, if enrichment is insufficient during enrichment control after fuel cut mode release, an erroneous determination of a failure in the downstream side oxygen concentration sensor 32 can be prevented because of failure determination prohibition by the failure determination prohibition device.

Embodiment 2

Figure 4:
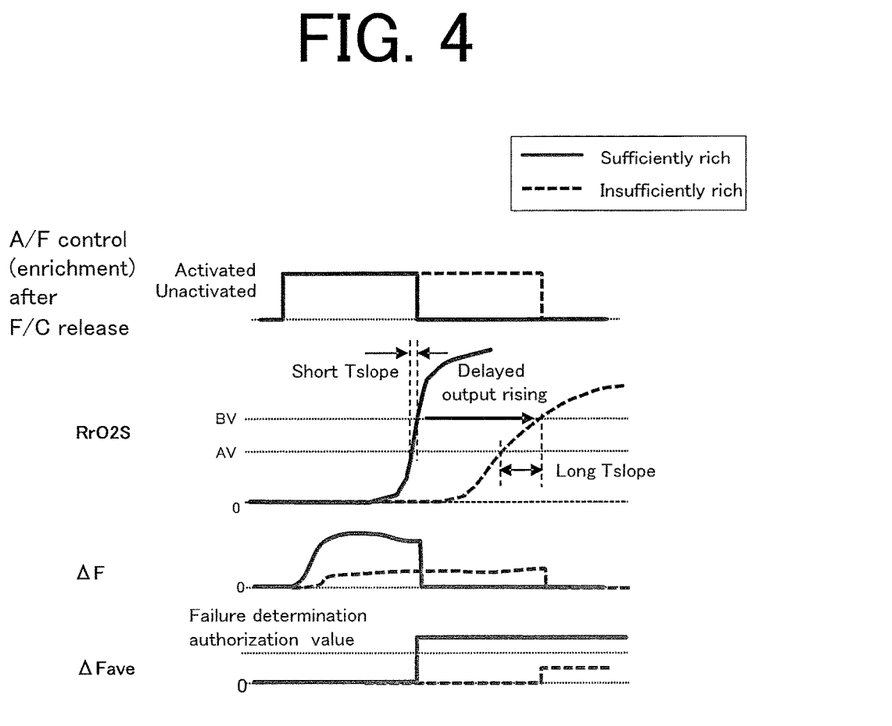
FIG. 4 is a time chart showing Embodiment 2.

FIG. 4 shows a time chart for illustrating failure determination prohibition according to Embodiment 2.

FIG. 4, like FIG. 2, is the time chart showing an example of changes in the output value V of the downstream side oxygen concentration sensor 32 in the enrichment control mode after release of the fuel cut mode, changes in the enriching fuel supply amount ΔF relative to the fuel supply amount necessary for stoichiometric combustion, and changes in the time average ΔFave of ΔF. Duplicate explanations for the same parts as in FIG. 2 will be omitted.

In the present embodiment, the failure determination prohibition device renders the value, which is set for failure determination authorization and defines the range where the failure determination prohibition device does not prohibit failure determination, small when enrichment is sufficient, and large when enrichment is insufficient. By so doing, determinations of failures other than actual failures can be prevented more reliably.

Figure 5:
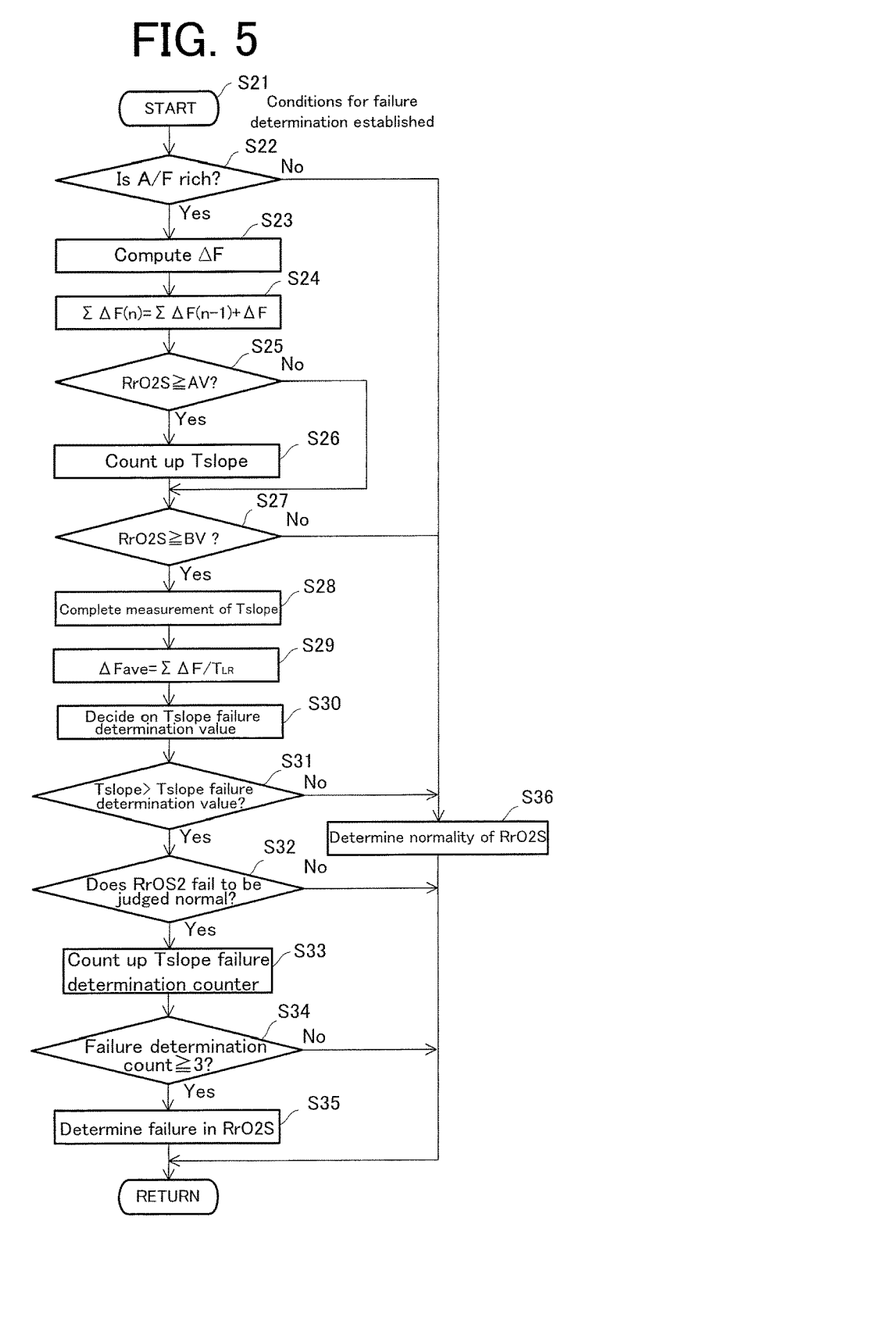
FIG. 5 is a flow chart of Embodiment 2.

The flow of failure determination according to the present embodiment will be described by reference to FIG. 5. As shown in FIG. 5, when conditions for failure determination are established in Step S21, it is determined in Step S22 whether the air-fuel ratio A/F is rich. If A/F is rich (Step S22: Yes), ΔF is computed in Step S23. If A/F is not rich (Step S22: No), it is determined in Step S36 that RrO2S, which is the downstream side oxygen concentration sensor 32, is normal. At this stage, the program terminates.

Then, in Step S24, ΣΔF(n) is obtained. Then, in Step S25, it is determined whether the output of the downstream side oxygen concentration sensor 32, RrO2S, is equal to or more than a predetermined value A, e.g., 0.3V. If RrO2S is equal to or more than the predetermined value AV (Step S25: Yes), Tslope is counted up in Step S26, and it is determined in Step S27 whether the output RrO2S of the downstream side oxygen concentration sensor 32 is equal to or more than a predetermined value B, e.g., 0.5V.

If, in Step S27, RrO2S is equal to or more than the predetermined value B, measurement of Tslope is completed in Step S28. Then, in Step S29, the time average ΔFave of ΔF is computed and, in Step S30, a Tslope failure determination value is decided on. The Tslope failure determination value is a map value determined by the value of ΔFave, and is set such that the smaller ΔFave, the higher the Tslope failure determination value is.

In Step S31, it is determined whether Tslope is greater than the Tslope failure determination value set in Step S30. If, in Step S31, Tslope is greater than the Tslope failure determination value (Step S31: Yes), it is determined in Step S32 whether RrO2S, which is the downstream side oxygen concentration sensor 32, is judged to be normal.

If, in Step S32, RrO2S is not judged to be normal (Step 32: Yes), the Tslope failure determination counter is counted up in Step S33. In Step S34, it is determined whether the failure determination count is equal to or more than 3. If the failure determination count is equal to or more than 3 (Step S34: Yes), it is determined in Step S35 that the downstream side oxygen concentration sensor 32 is failed. At this stage, the program terminates. If the failure determination count is smaller than 3 (Step S34: No), the program ends automatically, without determining a failure in the downstream side oxygen concentration sensor 32.

If, in Step 31, Tslope is smaller than the Tslope failure determination value (Step S31: No), it is determined in Step S36 that RrO2S, which is the downstream side oxygen concentration sensor 32, is normal. At this stage, the program terminates. If, in Step S32, RrO2S is judged to be normal (Step S32: No), the program ends automatically.

According to the flow described above, the Tslope failure determination value is variable, and the smaller ΔFave, the higher the Tslope failure determination value becomes. Under these conditions, a determination is made. Thus, unless ΔFave is equal to or more than the failure determination authorization value, failure determination is not authorized and, if Tslope is smaller than the Tslope failure determination value, a determination of a failure is not made. In the present embodiment, the Tslope failure determination value is rendered variable, but this is not limitative. If determination of a failure in the downstream side oxygen concentration sensor 32 is made based on the period until the output of the downstream side oxygen concentration sensor 32 after release of the fuel cut mode of the engine 1 reaches the predetermined output, a failure determination value concerned with the length of the period until the output of the oxygen concentration sensor during enrichment control after release may be rendered variable, and the smaller ΔFave, the higher the failure determination value may be made.

INDUSTRIAL APPLICABILITY

The present invention is applicable not only to gasoline engines of a cylinder fuel injection type as in the foregoing embodiments, but also to various internal combustion engines. The invention can be widely applied in determining failures in air-fuel ratio detectors arranged downstream of various catalyst provided in their exhaust systems.

EXPLANATION OF LETTERS OR NUMERALS

1 Engine
2 Intake passage
3 Exhaust passage
4 Fuel injection valve
10 Throttle valve
11 Throttle position sensor
12 Air flow sensor
20 Crank angle sensor
30 Exhaust purification catalyst
31 Upstream side oxygen concentration sensor
32 Downstream side oxygen concentration sensor
40 ECU

The invention claimed is:

1. A failure determination apparatus installed on a vehicle including an internal combustion engine, an injector for supplying fuel to a combustion chamber of the internal combustion engine, a catalyst provided in an exhaust system of the internal combustion engine, and an oxygen concentration sensor disposed downstream of the catalyst for outputting a value corresponding to an air-fuel ratio,
the failure determination apparatus comprising:
a processor and a memory storing instructions that causes the processor to,
stop a fuel injection by the injector into the internal combustion engine under a no-load condition,
perform an enrichment control after stoppage of the fuel injection by supplying fuel by the injector,
count, after the start of the enrichment control, a time taken for an output value of the oxygen concentration sensor to rise from a first value to a second value,
calculate, by using a fuel supply amount from the injector, a difference between an actual fuel supply amount during the enrichment control and a fuel supply amount necessary for stoichiometric combustion,
further calculate, by using the difference, an average amount of the difference within a predetermine time during the enrichment control,
determine, by using the time, that the oxygen concentration sensor is normal, if the time is equal to or less than a first determination value,
further determine, when the oxygen concentration sensor is not determined to be normal, a permission or a prohibition of executing a failure determination of the oxygen concentration sensor, by comparing the average amount with a second determination value, wherein the execution of failure determination of the oxygen concentration sensor is permitted if the average amount exceeds the second determination value, whereas the execution is prohibited if the average amount is equal to or less than the second determination value, and
conclude that the oxygen sensor is failed when the permission of the execution of failure determination of the oxygen concentration sensor is determined.

2. The failure determination apparatus according to claim 1, wherein
the instructions further cause the processor to restrict the failure determination of the failure determination device if the time average of the enriching fuel supply amount is equal to or less than the predetermined value.

3. The failure determination apparatus according to claim 1, wherein
the instructions further cause the processor to
generate a third determination value greater than the first determination value based on the average amount,
set the third determination value as a substitute for the first determination value, instead of permitting or prohibiting the execution failure determination based on the average value,
determine, by comparing the time with the third determination value, that the oxygen concentration sensor is normal, if the time is equal to or less than the third determination value, and
conclude that the oxygen concentration sensor is failed when the oxygen concentration sensor is not determined to be normal.

4. The failure determination apparatus according to claim 2, wherein
the instructions further cause the processor to determine the failure if the length of the period when the output of the oxygen concentration sensor during the enrichment control passes through the predetermined output section is greater than a predetermined failure determination value.

5. The failure determination apparatus according to claim 3, wherein
the instructions further cause the processor to set the failure determination value of the failure determination device to be high if the time average of the enriching fuel supply amount is equal to or less than the predetermined value.

6. The failure determination apparatus according to claim 4, wherein
the instructions further cause the processor to set the failure determination value of the failure determination device to be high if the time average of the enriching fuel supply amount is equal to or less than the predetermined value.

7. The failure determination apparatus according to claim 1, wherein
the instructions further cause the processor to,
make failure determination if the length of the period until the output of the oxygen concentration sensor during enrichment control after the release of the fuel cut mode reaches the predetermined output is greater than a predetermined failure determination value, and
set the failure determination value of the failure determination device to be high if the time average of the enriching fuel supply amount is equal to or less than the predetermined value.

* * * * *